United States Patent [19]

Wyss et al.

[11] Patent Number: 4,981,996

[45] Date of Patent: Jan. 1, 1991

[54] METHOD FOR THE PRODUCTION OF O-SUBSTITUTED HYDROXYLAMINES

[75] Inventors: Heinz Wyss, Heimberg; Hans P. Mettler, Brig-Glis; Felix Previdoli, Brig, all of Switzerland

[73] Assignee: Lonza Ltd., Basel, Switzerland

[21] Appl. No.: 348,055

[22] Filed: May 5, 1989

[30] Foreign Application Priority Data

May 11, 1988 [CH] Switzerland .......................... 1778/88

[51] Int. Cl.$^5$ ................... C07C 239/00; C07C 259/00
[52] U.S. Cl. ..................................... 564/300; 564/301
[58] Field of Search ................................ 564/300, 301

[56] References Cited

U.S. PATENT DOCUMENTS 3,491,151  1/1970  Bader .................................. 564/300

Primary Examiner—Richard L. Raymond
Assistant Examiner—Raymond Covington
Attorney, Agent, or Firm—Horst M. Kasper

[57] ABSTRACT

A new method for the production of O-substituted hydroxylamines is disclosed. Hydroxylamine-O-sulfonic acid is reacted with alkali alkoxide in the presence of a polar aprotic solvent.

22 Claims, No Drawings

METHOD FOR THE PRODUCTION OF O-SUBSTITUTED HYDROXYLAMINES

BACKGROUND OF THE INVENTION

1. Field of the Invention

The invention relates to a method for the production of O-substituted hydroxylamines.

2. Brief Description of the Background of the Invention Including Prior Art

It has been known for a long time to produce O-substituted hydroxylamines from hydroxylamine-O-sulfonic acid by reaction with a corresponding alkali alkoxide in the presence of an alcohol (Rendiconti 1965, Volume 38, p. 589 ff., Volume 39, p. 83 ff.). The maximum yields obtained according to this method are at best 50%. In addition, it is a particular disadvantage of this reaction that in many cases non-reacted, explosive hydroxylamine-O-sulfonic acid is present as an alkali salt in the reaction mixture. The consequently required processing by filtration is not suitable for a large-scale technical production. In addition, products produced according to this method have to be purified based on their impurity by way of recrystallization.

SUMMARY OF THE INVENTION

1. Purposes of the Invention

It is an object of the present invention to avoid the disadvantages associated with the conventional production of hydroxylamine-O-alcoholates.

It is a further object of the present invention to provide a method for the production of O-substituted hydroxylamines for furnishing higher yields.

It is yet a further object of the present invention to provide a production method for O-substituted hydroxylamines minimizing dangers associated with the presence of explosive materials and which method is suitable for a large-scale industrial production of such compounds.

These and other objects and advantages of the present invention will become evident from the description which follows.

2. Brief Description of the Invention

The present invention provides for a method for the production of O-substituted hydroxylamines. Hydroxylamine-O-sulfonic acid is reacted with an alkali alkoxide of the formula

wherein M=sodium or potassium and wherein R=$C_1$–$C_6$ alkyl or alkenyl, straight-chain or branched, substituted or unsubstituted, or benzyl, possibly substituted in a reaction mixture in the presence of a polar aprotic solvent employed as an additional solvent and of an alcohol ROH, wherein R has the meaning recited for obtaining an O-substituted hydroxylamine having the formula $NH_2$—O—R, with R defined as above.

The ratio of the alcohol ROH to the additional solvent can be maintained within a range of from about 1:1 to 1:10 by weight.

A solvent can be employed which can be selected from the group consisting of tetrahydrofuran, N,N-dimethyl formamide, acetonitrile, dibutyl ether, dimethyl acetamide, dimethyl sulfoxide, sulfolane, or diethylene glycol dimethyl ether, and mixtures thereof for the polar aprotic solvent.

The reaction temperature can be maintained at a range of temperatures from about 0° to 100° C.

The alkali alkoxide can be generated in situ from an alkali hydroxide MOH and an alcohol ROH, wherein M and R have the meaning recited above.

An alcohol ROH can be employed, wherein the R can comprise up to 8 carbon atoms in the molecule. An aprotic solvent can be employed having a boiling point above 80 degrees centigrade.

Preferably, the hydroxylamine-O-sulfonic acid dissolved in the additional solvent is furnished, and only then the corresponding alkali alkoxide dissolved in alcohol is added and reacted. The alkali alkoxide dissolved in alcohol can form a solution, which solution can further comprise the additional solvent.

Hydrochloric acid can be added to the reaction product containing the O-substituted hydroxylamine and the O-substituted hydroxylamine can be isolated as a hydrochloride.

The hydroxylamine-O-sulfonic acid can be added to the alkali alkoxide present. The resulting O-substituted hydroxylamine can be separated from the reaction during the addition. The alkali alkoxide can be employed in admixture with the additional solvent.

The novel features, which are considered as characteristic for the invention, are set forth in the appended claims. The invention itself, however, both as to its method of operation, its products and physical requirements, together with additional objects and advantages thereof, will be best understood from the following description of specific embodiments and examples.

DESCRIPTION OF INVENTION AND PREFERRED EMBODIMENT

In accordance with the present invention, there is provided a method for the production of O-substituted hydroxylamines according to the formula

wherein R=$C_1$–$C_6$ alkyl or alkenyl, straight-chain or branched, substituted or unsubstituted, or benzyl, possibly substituted, by reaction of hydroxylamine-O-sulfonic acid with an alkali alkoxide of the formula

wherein M=sodium or potassium and where R has the meaning recited, in the presence of an alcohol ROH, wherein R has the meaning recited, the improvement comprising that a polar aprotic solvent is employed as an additional solvent.

The polar aprotic solvent can be selected from the group consisting of tetrahydrofuran, N,N-dimethyl formamide, acetonitrile, dibutyl ether, N,N-dimethyl acetamide, dimethyl sulfoxide, sulfolane, or diethylene glycol dimethyl ether, and mixtures thereof.

The alkali alkoxide can be generated in situ from an alkali hydroxide MOH and an alcohol ROH, wherein M and R have the meaning recited above.

The alkali alkoxide or, respectively, the corresponding alkali hydroxide and the corresponding alcohol can be furnished to provide alkali alkoxide, wherein the hydroxylamine-O-sulfonic acid can be added and where, during the addition, the resulting O-substituted hydroxylamine can be separated from the reaction.

The alkali alkoxide or, respectively, the corresponding alkali hydroxide and the corresponding alcohol can be furnished together with the additional solvent.

Preferably, the hydroxylamine-O-sulfonic acid is furnished in the additional solvent and, only thereupon, the corresponding alkali alkoxide, dissolved in alcohol, is added and reacted. The alkali alkoxide dissolved in alcohol can further comprise the additional solvent in the solution.

The O-substituted hydroxylamine can be isolated by the addition of hydrochloric acid as a hydrochloride.

According to the invention, hydroxylamine-O-sulfonic acid is reacted with an alkali alkoxide of the formula

M—O—R wherein M=sodium or potassium, and where R=$C_1$-$C_6$ alkyl or alkenyl, substituted or unsubstituted, straight-chain or branched, or benzyl, possibly substituted, and reacting, according to the invention, in a polar aprotic solvent as an additional solvent for the production of O-substituted hydroxylamines of the formula

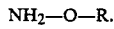

$NH_2$—O—R.

Preferred representatives of the $C_1$-$C_6$ alkyl groups include, for example, methyl or ethyl groups. In addition, propyl, butyl, pentyl, and hexyl groups, branched or straight-chain, can be employed. Preferred representatives of the alkenyl group are the allyl or the crotyl groups, but also butenol-1, butenol-2, butenol-3, or pentenol or hexenol can be employed. The substituents of the alkyl or alkylene groups can include substituted amino groups such as, for example, dialkyl amino groups, in particular dimethyl amino, diethyl amino, dipropyl amino groups. The benzyl group is preferably unsubstituted. Possible substituents of the benzyl group can include halogen atoms such as chlorine and bromine, nitro groups or alkyl groups, including methyl, ethyl, propyl, isopropyl, butyl, isobutyl, and tertiary butyl, alkyl with up to 20 carbon atoms and, preferably, with up to 6 carbon atoms, cycloalkyl with up to 8 carbon atoms.

The hydroxylamine-O-sulfonic acid can be produced in a conventional way from hydroxylamine sulfate by treating with oleum, as taught in "Inorganic Synthesis," Volume 5, p. 122, 1957.

According to the invention, tetrahydrofuran, N,N-dimethyl formamide, acetonitrile, dibutyl ether, N,N-dimethyl acetamide, dimethyl sulfoxide, sulfolane, or diethylene glycol dimethyl ether, hexamethyl phosphorus triamide, are suitable as additional solvents. Particular advantageous as additional solvents are acetonitrile, sulfolane, or N,N-dimethyl acetamide. Aprotic solvents are solvents which do not contain ionizable protons in their molecules.

The ratio of additional solvent to alcohol can advantageously be between 1:1 and 10:1, and is preferably between 3:1 and 5:1. The weight amount of the aprotic solvent in the reactive mixture should be initially at least about 30 weight-percent, is preferably at least about 50 weight-percent, and can be more than 60 weight-percent of the reaction mixture.

Advantageously the hydroxylamine-O-sulfonic acid is contained in the additional solvent and then alkali alkoxide or alcoholate with the corresponding alcohol is added over a certain period of time.

According to a further variation, the dissolved alkali alkoxide can possibly be presented in the additional solvent and then the hydroxylamine-O-sulfonic acid can be added. During this addition, the resulting O-substituted hydroxylamine can be removed from the reaction, for example, by distillation. This latter variation of the method is preferred for the method as employed on an industrial scale. It is further possible to generate the alkali alkoxide in situ from the corresponding alkali hydroxide MOH and the alcohol ROH, wherein R and M have the meaning recited.

The reaction temperature can usually be between 0° and 100° C. for the preferred compounds with R=methyl or ethyl, and preferably between 15° and 30° C., depending on the substituent R selected.

After a reaction time of from about two to five hours, the reaction product is advantageously separated by distillation from the reaction mixture.

It is an advantage to convert the obtained O-substituted hydroxylamine with, for example, hydrochloric acid directly into the corresponding hydrochloride and, as a rule, to isolate this hydrochloride as a solid product.

It is particularly advantageous according to the invention method that the O-alkyl hydroxylamine, in particular the O-methyl and the O-ethyl hydroxylamine, can be produced in yields of up to about 80%.

EXAMPLE 1

Production of Methoxyamine-HCl in Acetonitrile

A solution of 162.06 g (3.0 mol) sodium methylate in 378 g methanol was dropped to 113.09 g (1.0 mol) hydroxylamine-O-sulfonic acid, suspended in 1200 g acetonitrile, within 30 minutes and at a temperature of less than 10° C. The suspension was stirred for three hours at a temperature of 20° C. and the resultant methoxyamine was distilled off at a temperature of 40° C. and under a pressure of 200 mbar. The distillate was set to a pH value of 1 with 150 ml concentrated hydrochloric acid. The solution was concentrated by evaporation and dried for two hours under vacuum. 64.3 g product with a yield of 77%, as referred to the hydroxylamine-O-sulfonic acid, were obtained.

Melting point: 145° C.

Elementary analysis for $CH_5NO.HCl$ calculated: C 14.4%, H 7.2%, N 16.8%, found: C 13.8%, H 7.3%, N 17.1%.

EXAMPLE 2

Production of Methoxyamine-HCl in Dimethyl Formamide

Within 30 minutes, a solution of 162.06 g (3.0 mol) sodium methylate in 378 g methanol was dropped into 113.09 g (1.0 mol) hydroxylamine-O-sulfonic acid, suspended in 1425 g dimethyl formamide. This suspension was stirred for three hours at 20° C. and the generated methoxyamine was distilled off at a temperature of 40° C. and under a pressure of 200 mbar. The distillate was set to pH value of 1 with 150 ml of concentrated hydrochloric acid and was evaporated and dried for two hours under vacuum. 34.6 g of product with a yield of 43%, as referred to hydroxylamine-O-sulfonic acid, were obtained.

EXAMPLE 3

Production of Ethoxyamine-HCl

A solution of 272.2 g (4.0 mol) sodium ethylate in 1008 g ethanol was added to 113.9 g (1.0 mol) hydroxylamine-O-sulfonic acid, suspended in 1582 g acetonitrile, within 55 minutes and at a temperature of less than 10° C. Stirring was performed for five hours at a temperature of 20° C. The resultant ethoxyamine was distilled off at a temperature of 40° C. and under a pressure of 200 mbar and was set to a pH value of 1 with 150 ml of concentrated hydrochloric acid. The ethoxyamine was totally concentrated by evaporation and dried for two hours under vacuum. 69.6 g product, with a yield of 71%, as referred to the hydroxylamine-O-sulfonic acid, was obtained. The product can be further purified by recrystallization from ethanol/acetonitrile.

Melting point: 125°–128° C.

Elementary analysis for $C_2H_7NO \cdot HCl$: calculated: C 24.6%, H 8.3%, N 14.4%, found: C 24.3%, H 8.5%, N 14.9%.

EXAMPLE 4

Production of Isopropoxyamine-HCl

A suspension of 246.24 g (3.0 mol) sodium isopropylate in 1500 g isopropanol was added to 113.09 g (1.0 mol) hydroxylamine-O-sulfonic acid, suspended in 2500 g acetonitrile, within 30 minutes, at a temperature of less than 10° C. Then stirring was performed for six hours at a temperature of 50°–70° C. The generated isopropoxyamine was distilled off at a temperature of 50° C. and under a pressure of 200 mbar and was set to a pH value of 1 with 66.6 g concentrated hydrochloric acid HCl. Then a total concentration by evaporation was performed and drying occurred for two hours under vacuum. 55.7 g product with a yield of 50%, as referred to hydroxylamine-O-sulfonic acid, were obtained. The product can be further purified by recrystallization from isopropanol/acetonitrile.

Melting point: 92°

Elementary analysis for $C_3H_9NO \cdot HCl$: calculated: C 32.3%, H 9.0%, N 12.6% found: C 31.9%, H.9.6%%, N 13.2%.

EXAMPLE 5

Production of Crotyloxyamine-HCl

A solution of 282.27 g (3.0 mol) sodium crotylate in 788 g crotyl alcohol was added to 113.09 g (1.0 mol) hydroxylamine-O-sulfonic acid, suspended in 1582 g acetonitrile, within 30 minutes, at a temperature of less than 10° C. The resulting mixture was stirred for three hours at a temperature of 30° C. The resultant crotyloxyamine was distilled off at a temperature of 50° C. and under a pressure of 100 mbar and was set to a pH value of 1 with 150 ml concentrated hydrochloric acid HCl. Then total concentration by evaporation was performed and drying occurred for two hours under vacuum. 85.5 g product with a yield of 69%, as referred to hydroxylamine-O-sulfonic acid, were obtained.

Melting point: 178°–180° C.

Elementary analysis for $C_4H_9NO \cdot HCl$;

calculated: C 38.9%, H 8.2%, N 11.3%, found: C 37.6%, H 8.3%, N 11.6%.

EXAMPLE 6

Production of Benzyloxyamine-HCl

A solution of 390.36 g (3.0 mol) sodium benzylate in 1960 benzyl alcohol was dropped into 113.09 g (1.0 mol) hydroxylamine-O-sulfonic acid, suspended in 500 g acetonitrile, within one hour, at a temperature of 20° C. The resulting mixture was stirred for three hours at a temperature of 70° C. The acetonitrile and then the resultant benzyloxyamine was distilled off at a temperature of 50° C. and under a pressure of 1 mbar and was set to a pH value of 1 with 150 ml concentrated hydrochloric acid. Then total concentration by evaporation was performed and the product was dried for two hours under vacuum. 69.9 g product with a yield of 60%, as referred to hydroxylamine-O-sulfonic acid, were obtained. The product can additionally be purified by recrystallization from methanol.

Melting point: 230°–235° C. under decomposition

Elementary analysis for $C_7H_9NO \cdot HCl$: calculated: C 52.7%, H 6.3%, N 8.8%, found: C 52.5%, H 6.4%, N 9.1%.

EXAMPLE 7

Production of Ethoxyamine-HCl

A solution of 11.80 g (100 mmol) hydroxylamine-O-sulfonic acid in 350 ml ethanol was added to a suspension of 10.20 g (250 mmol) sodium hydroxide in 20 ml ethanol and 100 ml sulfolane, within a time period of two hours, at a temperature of 35° to 45° C. and under a pressure of 80 to 100 mbar. The distilled-off mixture of ethoxyamine and ethanol was furnished with 28 g concentrated hydrochloric acid and was concentrated by evaporation. 6.8 g product were obtained with a yield of 69%, as referred to hydroxylamine-O-sulfonic acid.

Melting point: 125°–128° C.

It will be understood that each of the steps, conditions and reagents described above, or two or more together, may also find a useful application in other types of reactions involving substituted hydroxylamines, in alkoxylation procedures and in products differing from the types described above.

While the invention has been illustrated and described as embodied in the context of a method for production of O-substituted hydroxylamines, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for the production of O-substituted hydroxylamines comprising reacting hydroxylamine-O-sulfonic acid with an alkali alkoxide of the formula

M—O—R wherein M=sodium or potassium and wherein R=$C_1$–$C_6$ alkyl or alkenyl, straight-chain or branched, substituted or unsubstituted, or benzyl, possibly substituted in a reaction mixture in the presence of a polar aprotic solvent and of an alcohol ROH, wherein R has the meaning recited for obtaining an O-substituted hydroxylamine having the formula NH$_2$—O—R, with R defined as above.

2. The method according to claim 1, further comprising
maintaining the ratio of the alcohol ROH to the additional solvent within a range of from about 1:1 to 1:10 by weight.

3. The method according to claim 1, further comprising
employing a solvent selected from the group consisting of tetrahydrofuran, N,N-dimethyl formamide, acetonitrile, dibutyl ether, N,N-dimethyl acetamide dimethyl sulfoxide, sulfolane, or diethylene glycol dimethyl ether, and mixtures thereof for the polar aprotic solvent.

4. The method according to claim 1, further comprising
maintaining the reaction temperature at a range of temperatures from about 0° to 100° C.

5. The method according to claim 1, further comprising
generating the alkali alkoxide in situ from an alkali hydroxide MOH and an alcohol ROH, wherein M and R have the meaning recited above.

6. The method according to claim 1, further comprising
employing an alcohol ROH, wherein the R comprises up to 8 carbon atoms in the molecule.

7. The method according to claim 1, further comprising employing an aprotic solvent having a boiling point above 80 degrees centigrade.

8. The method according to claim 1, further comprising
furnishing the hydroxylamine-O-sulfonic acid dissolved in the additional solvent, and only then adding and reacting the corresponding alkali alkoxide dissolved in alcohol.

9. The method according to claim 8, wherein the alkali alkoxide dissolved in alcohol forms a solution, which solution further comprises the additional solvent.

10. The method according to claim 1, further comprising
adding hydrochloric acid to the reaction product containing the O-substituted hydroxylamine;
isolating the O-substituted hydroxylamine as a hydrochloride.

11. The method according to claim 1, further comprising
adding the hydroxylamine-O-sulfonic acid to the alkali alkoxide present; and
separating the resulting O-substituted hydroxylamine from the reaction during the addition.

12. The method according to claim 11, further comprising
employing the alkali alkoxide in admixture with the additional solvent.

13. A method for the production of O-substituted hydroxylamines according to the formula

NH$_2$—O—R wherein R=C$_1$-C$_6$ alkyl or alkenyl, straight-chain or branched, substituted or unsubstituted, or benzyl, possibly substituted, by reaction of hydroxylamine-O-sulfonic acid with an alkali alkoxide of the formula

M—O—R wherein M=sodium or potassium and where R has the meaning recited, in the presence of an alcohol ROH, wherein R has the meaning recited, the improvement comprising that a polar aprotic solvent is employed as an additional solvent.

14. The method according to claim 13, wherein the ratio of the alcohol to the additional solvent is from about 1:1 to 1:10.

15. The method according to claim 13, wherein the polar aprotic solvent is selected from the group consisting of tetrahydrofuran, N,N-dimethyl formamide, acetonitrile, dibutyl ether, N,N-dimethyl acetamide dimethyl sulfoxide, sulfolane, or diethylene glycol dimethyl ether, and mixtures thereof.

16. The method according to claim 13, wherein the reaction temperature is maintained at a temperature from about 0° to 100° C.

17. The method according to claim 13, wherein the alkali alkoxide is generated in situ from an alkali hydroxide MOH and an alcohol ROH, wherein M and R have the meaning recited above.

18. The method according to claim 13, wherein the alkali alkoxide or, respectively, the corresponding alkali hydroxide and the corresponding alcohol are furnished to provide alkali alkoxide, wherein the hydroxylamine-O-sulfonic acid is added and where, during the addition, the resulting O-substituted hydroxylamine is separated from the reaction.

19. The method according to claim 13, wherein the alkali alkoxide or, respectively, the corresponding alkali hydroxide and the corresponding alcohol are furnished together with the additional solvent.

20. The method according to claim 13, wherein the hydroxylamine-O-sulfonic acid is furnished in the additional solvent and where only thereupon the corresponding alkali alkoxide, dissolved in alcohol, is added and reacted.

21. The method according to claim 20, wherein the alkali alkoxide dissolved in alcohol further comprises the additional solvent in the solution.

22. The method according to claim 13, wherein the O-substituted hydroxylamine is isolated by the addition of hydrochloric acid as a hydrochloride.

* * * * *